| United States Patent [19] | [11] | 4,227,971 |
|---|---|---|
| Zimmerschied | [45] | Oct. 14, 1980 |

[54] BROMINE REMOVAL FROM ACETIC ACID

[75] Inventor: Wilford J. Zimmerschied, Naperville, Ill.

[73] Assignee: Standard Oil Company (Indiana), Chicago, Ill.

[21] Appl. No.: 970,222

[22] Filed: Dec. 18, 1978

[51] Int. Cl.² ................... B01D 3/00; C07C 51/44; C07C 53/08
[52] U.S. Cl. ..................... 203/32; 203/33; 203/37; 562/414; 562/549; 562/608
[58] Field of Search ............ 562/414, 549, 608, 606; 203/37, 32, 33

[56] References Cited

U.S. PATENT DOCUMENTS

| 2,884,451 | 4/1959 | Graham | 562/549 |
|---|---|---|---|
| 3,084,109 | 4/1963 | Ure et al. | 562/549 |

*Primary Examiner*—Vivian Garner
*Attorney, Agent, or Firm*—Fred R. Ahlers; William T. McClain; William H. Magidson

[57] ABSTRACT

Concentrated acetic acid of 95 to 100 weight percent concentration containing both ionic and coordinate bromine can be successfully purified to a bromine content of less than 3 ppm by the sequential steps of catalytic hydrogenation, contacting the resulting acetic acid with alkali metal hydroxide, carbonate or bicarbonate, and then distilling acetic acid from the alkali metal.

4 Claims, No Drawings

BROMINE REMOVAL FROM ACETIC ACID

FIELD OF INVENTION

This invention relates to the removal of bromine from acetic acid and more specifically pertains to the removal of bromine from acetic acid obtained by the catalytic liquid phase oxidation of butane in the presence of catalysis provided by a combination of a source of bromine with one or more transition metal oxidation catalyst, more specifically cobalt, manganese or cobalt and manganese.

PRIOR ART BACKGROUND

According to U.S. Pat. No. 3,293,292 it is essential for the preparation of acetic acid to use both manganese and cobalt (e.g., in their 2+ form acetate tetrahydrates) with a source of bromine (e.g., ammonium bromide) to oxidize butane with oxygen gas in the liquid phase at 176°–177° C. and a gauge pressure of 65.4 kg/cm² in the presence of acetic acid as reaction solvent.

More recently U.S. Pat. No. 4,111,986 discloses that acetic acid can be prepared by contacting a sufficient concentration of oxygen-containing gas (e.g., oxygen gas at at least 5 liters per hour per 100 grams of butane) with normal liquid butane in the presence of an acetic acid solution of components of catalysis consisting essentially of cobalt (e.g., 1 to 50 milliequivalents per mole of butane) and bromine (2 to 500 milliequivalents per mole of butane). For this process reaction temperatures of at least 176°–177° C. are preferred at gauge pressures of from 35 up to 211 kg/cm², preferably from 56 up to 105.5 kg/cm².

Concentrated acetic acid (even glacial) distilled from the effluent produced by the foregoing liquid phase oxidation processes is contaminated with bromine-containing compounds, and is not generally suitable as an article of commerce even though the commercial specifications for glacial acetic acid or acetic anhydride do not set a maximum allowable value for a bromine concentration.

Also acetic acid becomes contaminated with bromides when used as solvent or reaction medium for the liquid phase oxidation of alkyl-substituted aromatic compounds (e.g., xylenes, toluene, trimethyl benzenes) with air to the corresponding aromatic carboxylic acid in the presence of catalysis provided by the components comprising a combination of one or more transition metal oxidation metal catalysts and a source of bromine (e.g., $Br_2$, HBr, inorganic bromide salt, an organic bromide such as tetrabromoethane). While some who practice such process for the production of aromatic carboxylic acids reuse the bromide contaminated acetic acid in the alkyl aromatic oxidation process, others (e.g., the assignee of U.S. Pat. No. 3,578,706) prefer to remove the bromine or bromine-containing contaminants before reusing the acetic acid in the oxidation process.

According to said U.S. Pat. No. 3,578,706 the bromine contaminated acetic acid is treated by reaction with a metal having electrochemical potential between manganese and iron, inclusive and then contacting the acetic acid with an anion exchanger to remove the bromine or bromides.

Such bromine contaminated acetic acids can contain both ionic and coordinate forms of bromine (e.g., bromine attached to carbon) which are not entirely removed by distillation or fractionation but rather carry through to the 97–100% acetic acid fraction in amounts of from 0.0005 up to 0.015 weight percent total of said two forms of bromine. We have found that by a simple two step process the concentrated acetic acid can be purified to a bromine content below the present capability of analytical detectability which is, on a weight basis, 3 parts bromine per $1 \times 10^6$ parts (i.e., 3 ppm) acetic acid.

STATEMENT OF THE INVENTION

The foregoing removal of bromine to a concentration of less than 3 ppm by weight bromine on acetic acid can be accomplished by (a) contacting the concentrated (95 to 100 weight percent) acetic acid contaminated with from 0.0005 up to 0.015 weight percent bromine and hydrogen gas with a palladium catalyst, preferably such catalyst having palladium crystallites dispersed on the surface of activated carbon and (b) then contacting the concentrated acetic acid with an alkali metal hydroxide, carbonate or bicarbonate. The acetic acid is separated from the alkali metal compound, preferably by distillation.

Such palladium on activated carbon (Pd/C) catalyst can have, on a weight basis, from 0.01 up to 1.0 percent palladium. The activated carbon should have a high surface area per unit of mass that is desirably 800 m²/g and preferably 1000 to 3000 m²/g, and a low extraneous metal content.

The step of contacting the bromine contaminated concentrated acetic acid and hydrogen with Pd/C catalyst can be conducted with the acetic acid in the liquid phase or the vapor phase. Where liquid phase operation is selected, it can be carried out at a temperature of at least 50° C. and up to 120° C. with a hydrogen partial pressure of from 0.35 up to 7 kg/cm² which will, at temperatures above 115° C., maintain the acetic acid in the liquid phase. Such contacting can be by maintaining a suspension of particulate catalyst in the liquid acetic acid or by passing the liquid acetic acid upward or downward through a bed of particulate catalyst and passing a hydrogen concurrent with or countercurrent to the liquid acetic acid.

The step of contacting the mixture of hydrogen and acetic acid with the Pd/C catalyst can be conducted with a vapor phase of the contaminated acetic acid. For example, bromine contaminated acetic acid is vaporized, hydrogen gas is added thereto and the vapor-gas mixture passed upward or downward through particulate (2 to 20 mesh U.S. Standard Sieve) catalyst. Such vapor phase contacting with Pd/C catalyst can be conducted at a temperature of from 115° C. up to 125° C. with a hydrogen concentration represented by a partial pressure of from 0.35 up to 7 kg/cm².

The amount of alkali metal hydroxide, carbonate or bicarbonate to be used is from 1 to 100 equivalent weights per equivalent weight of bromine contaminant originally present. The use of alkali metal carbonate or bicarbonate is preferred because, unlike the use of the hydroxide, it will not add water to the concentrated acetic acid. The contacting with the alkali metal compound is preferably carried out at a temperature of from 20° up to 50° C. although the temperature of this contacting is not critical with respect to speed or effect of contacting.

A single lot of bromine contaminated concentrated (99 weight percent) acetic acid containing 58 ppm total of ionic and coordinate bromine is used in the following three (two Comparative and one Illustrative) examples.

COMPARATIVE EXAMPLE I

Forty grams of the 58 ppm bromine contaminated concentrated acetic acid is mixed with 2.0 grams of potassium hydroxide and then acetic acid is removed by distillation. The bromine content of the recovered concentrated acetic acid condensate is found by X-ray diffraction analysis, to contain 17 ppm bromine.

COMPARATIVE EXAMPLE II

To a Fisher-Porter Bottle there is charged 50 grams of the 58 ppm bromine contaminated concentrated acetic acid and 5 grams of Pd/C catalyst containing 0.5 weight percent palladium as crystallites on the surface of activated carbon of low metal content having a surface to unit mass ratio of 1100 $m^2/g$. The catalyst particles are 4×8 mesh (U.S. Standard Sieve) in size. The bottle is pressured with hydrogen to a gauge pressure of 1.75 $kg/cm^2$. Thereafter the contents of the bottle are stirred and heated to a temperature of 100° C. and held at that temperature for 2 hours. Thereafter the treated acetic acid is separated from the catalyst by filtration and analyzed by X-ray diffraction. The recovered acetic acid is found to have a bromine content of 20 ppm.

ILLUSTRATIVE EXAMPLE 1

The method of Comparative Example II is repeated except the hydrogen pressure is 3.5 $kg/cm^2$ and the reaction temperature is 50° C. Thereafter the concentrated acetic acid so treated is mixed with two grams of potassium carbonate and then distilled therefrom. The condensate of concentrated acetic acid recovered is found, by X-ray diffraction analysis, to contain less than 3 ppm of bromine.

The invention claimed is:

1. The method of removing bromine from acetic acid of 95 to 100 weight percent concentration contaminated with ionic and coordinate bromine in a total amount of from 0.0005 to 0.015 weight percent by contacting hydrogen and said contaminated acetic acid with a palladium catalyst having palladium crystallites dispersed on the surface of low extraneous metal content activated carbon having a surface to mass ratio of at least 800 $m^2/g$, separating the acetic acid from said catalyst, contacting the separated acetic acid with an alkali metal hydroxide, carbonate or bicarbonate, and distilling the acetic acid from said alkali metal compound.

2. The method of claim 1 wherein the palladium catalyst is contacted with the contaminated acetic acid in the vapor phase.

3. The method of claim 1 wherein the palladium catalyst in particulate form is contacted with the contaminated acetic acid in the liquid phase and thereafter the separated acetic acid is contacted with potassium hydroxide and is distilled therefrom.

4. The method of claim 3 wherein the palladium catalyst contains 0.5 weight percent palladium.

* * * * *